(12) United States Patent
Jin et al.

(10) Patent No.: US 11,375,979 B2
(45) Date of Patent: Jul. 5, 2022

(54) ULTRASONIC PROBE

(71) Applicant: SAMSUNG MEDISON CO., LTD., Gangwon-do (KR)

(72) Inventors: Gil Ju Jin, Seoul (KR); Ji Ho Gu, Seongnam-si (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 113 days.

(21) Appl. No.: 16/823,850

(22) Filed: Mar. 19, 2020

(65) Prior Publication Data
US 2020/0297315 A1   Sep. 24, 2020

(30) Foreign Application Priority Data

Mar. 21, 2019   (KR) .......................... 10-2019-0032169

(51) Int. Cl.
*A61B 8/00* (2006.01)

(52) U.S. Cl.
CPC .......... *A61B 8/4466* (2013.01); *A61B 8/4483* (2013.01); *A61B 2562/187* (2013.01)

(58) Field of Classification Search
CPC . F16L 53/00; F16L 53/70; F16L 53/75; A61B 8/44; A61B 8/4466; A61B 8/4444; A61B 8/56; A61B 2562/187; A61B 2562/182; A61B 2562/22; A61B 2562/221; A61B 2562/225; A61B 2562/227;

(Continued)

(56) References Cited

U.S. PATENT DOCUMENTS

| 6,068,622 | A | 5/2000 | Sater et al. |
| 2015/0217141 | A1* | 8/2015 | Barthe .................... A61N 7/02 601/2 |

(Continued)

FOREIGN PATENT DOCUMENTS

| KR | 10-2010-0047395 A | 5/2010 |
| KR | 10-2015-0025383 A | 3/2015 |

(Continued)

OTHER PUBLICATIONS

Thermal Conductivity of materials and metals (www.engineeringtoolbox.com, retrieved Sep. 3, 2021).*

(Continued)

*Primary Examiner* — Carolyn A Pehlke
(74) *Attorney, Agent, or Firm* — Morgan, Lewis & Bockius LLP

(57) ABSTRACT

Disclosed is an ultrasonic probe having an improved heat radiation capability. The ultrasonic probe includes a transducer module configured to transmit and receive an ultrasonic signal, a housing configured to accommodate the transducer module, a cable connected to the transducer module inside the housing and drawn from the inside of the housing to the outside of the housing through an end of the housing, a bending device configured to cover the cable and connected to the end of the housing to receive heat, a strain relief configured to surround the bending device and including a heat radiation groove extending along a circumferential direction of the cable, and a heat radiation fin inserted into the heat radiation groove such that one end thereof is in contact with the bending device and the other end thereof is in contact with outside air.

17 Claims, 12 Drawing Sheets

(58) Field of Classification Search
CPC ... H05B 3/08; H05B 3/10; H05B 3/12; H05B 3/18; H05B 3/54; H05B 3/56
See application file for complete search history.

(56) References Cited

U.S. PATENT DOCUMENTS

2015/0253290 A1   9/2015   Fujii et al.
2018/0100614 A1   4/2018   Watanabe et al.

FOREIGN PATENT DOCUMENTS

KR   10-2017-0126418 A   11/2017
KR   10-1814172 B1       1/2018
WO   2015/147355 A1      10/2015

OTHER PUBLICATIONS

Extended European Search Report issued in corresponding European Patent Application No. 20155068.8 dated Aug. 18, 2020.

\* cited by examiner

ULTRASONIC PROBE

CROSS-REFERENCE TO RELATED APPLICATION(S)

This application is based on and claims priority under 35 U.S.C. § 119 to Korean Patent Application No. 10-2019-0032169, filed on Mar. 21, 2019, in the Korean Intellectual Property Office, the disclosure of which is incorporated by reference herein in its entirety.

BACKGROUND

1. Field

The disclosure relates to relates to an ultrasonic probe for generating an image of the inside of an object using ultrasonic waves, and more particularly, to an ultrasonic probe having an improved heat radiation capability.

2. Description of Related Art

An ultrasonic imaging apparatus is an apparatus that irradiates an ultrasonic signal from a body surface of an object toward a target site in the body and obtains an image of a monolayer or blood flow of soft tissue without invasion by using information of a reflected ultrasonic signal (ultrasonic echo signal).

The ultrasonic imaging apparatus is small, inexpensive, real-time displayable, and has a high level of safety because there is no radiation exposure, compared to other imaging diagnostic apparatuses such as an X-ray diagnostic apparatus, an X-ray CT scanner (Computerized Tomography Scanner), an MRI (Magnetic Resonance Image) and a nuclear medicine diagnostic apparatus, and thus, the ultrasonic imaging apparatus has been widely used for diagnosis of the heart, abdomen, urinary system and obstetrics.

The ultrasonic imaging apparatus includes an ultrasonic probe for transmitting an ultrasonic signal to an object to obtain an ultrasonic image of the object and receiving an ultrasonic echo signal reflected from the object, and a main body for generating an image of the inside of the object using the ultrasonic echo signal received from the ultrasonic probe.

In general, a line for connecting the ultrasonic probe and the main body is provided between the ultrasonic probe and the main body. This is called a wired ultrasonic imaging apparatus. The wired ultrasonic imaging apparatus may include a strain relief capable of reducing a load on a broken portion when a cable is bent or twisted.

SUMMARY

It is an aspect of the disclosure to provide an ultrasonic probe having an improved heat radiation capability.

It is another aspect of the disclosure to provide an ultrasonic probe having an improved heat radiation capability by heat radiation fins while maintaining a flexible property of a strain relief by forming heat radiation grooves on the strain relief and positioning the heat radiation fins in the heat radiation grooves.

Additional aspects of the disclosure will be set forth in part in the description which follows and, in part, will be obvious from the description, or may be learned by practice of the disclosure.

In accordance with an aspect of the disclosure, an ultrasonic probe includes a transducer module configured to transmit and receive an ultrasonic signal, a housing configured to accommodate the transducer module, a cable connected to the transducer module inside the housing and drawn from the inside of the housing to the outside of the housing through an end of the housing, a bending device configured to cover the cable and connected to the end of the housing to receive heat, a strain relief configured to surround the bending device and including a heat radiation groove extending along a circumferential direction of the cable, and a heat radiation fin inserted into the heat radiation groove such that one end thereof is in contact with the bending device and the other end thereof is in contact with outside air.

The bending device may be configured to be bendable in a first direction and in a second direction crossing the first direction.

The bending device and the heat radiation fin may be configured to have a higher thermal conductivity than the strain relief.

The strain relief may be made of a flexible material to be bendable in all directions.

The ultrasonic probe may further include a heat radiation frame disposed inside the housing and adjacent to the end of the housing and configured to receive heat generated in the housing.

The bending device may be disposed such that at least a portion thereof is in contact with the heat radiation frame.

The strain relief may further include a cutout portion formed on one surface of the heat radiation groove to increase a contact area between the heat radiation fin and outside air.

The strain relief may further include a bending groove formed by recessing a portion of an outer surface of the strain relief to enhance the flexibility of the strain relief.

The bending device may include a first bending member including a hollow portion through which the cable passes, and a second bending member including a hollow portion through which the cable passes and coupled to the first bending member to be rotatable in a first direction and in a second direction crossing the first direction with respect to the first bending member.

The first bending member and the second bending member may be repeatedly arranged along a direction in which the cable extends.

In accordance with another aspect of the disclosure, an ultrasonic probe includes a transducer module configured to transmit and receive an ultrasonic signal, a housing configured to accommodate the transducer module, a cable connected to the transducer module inside the housing and drawn from the inside of the housing to the outside of the housing through an end of the housing, a mesh member configured to surround the cable and to be bendable in all direction, a strain relief configured to surround an outer surface of the mesh member and including a heat radiation groove extending along a circumferential direction of the cable, and a heat radiation fin inserted into the heat radiation groove such that one end thereof is in contact with the mesh member and the other end thereof is in contact with outside air.

The ultrasonic probe may further include a heat radiation frame disposed inside the housing and adjacent to the end of the housing and configured to receive heat generated in the housing.

The mesh member may be disposed such that at least a portion thereof is in contact with the heat radiation frame.

The strain relief may further include a cutout portion formed on one surface of the heat radiation groove to increase a contact area between the heat radiation fin and outside air.

The strain relief may further include a bending groove formed by recessing a portion of an outer surface of the strain relief to enhance the flexibility of the strain relief.

The mesh member and the heat radiation fin may be made of a metal material to have a higher thermal conductivity than the strain relief.

The strain relief may be made of a flexible material to be bendable in all directions.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
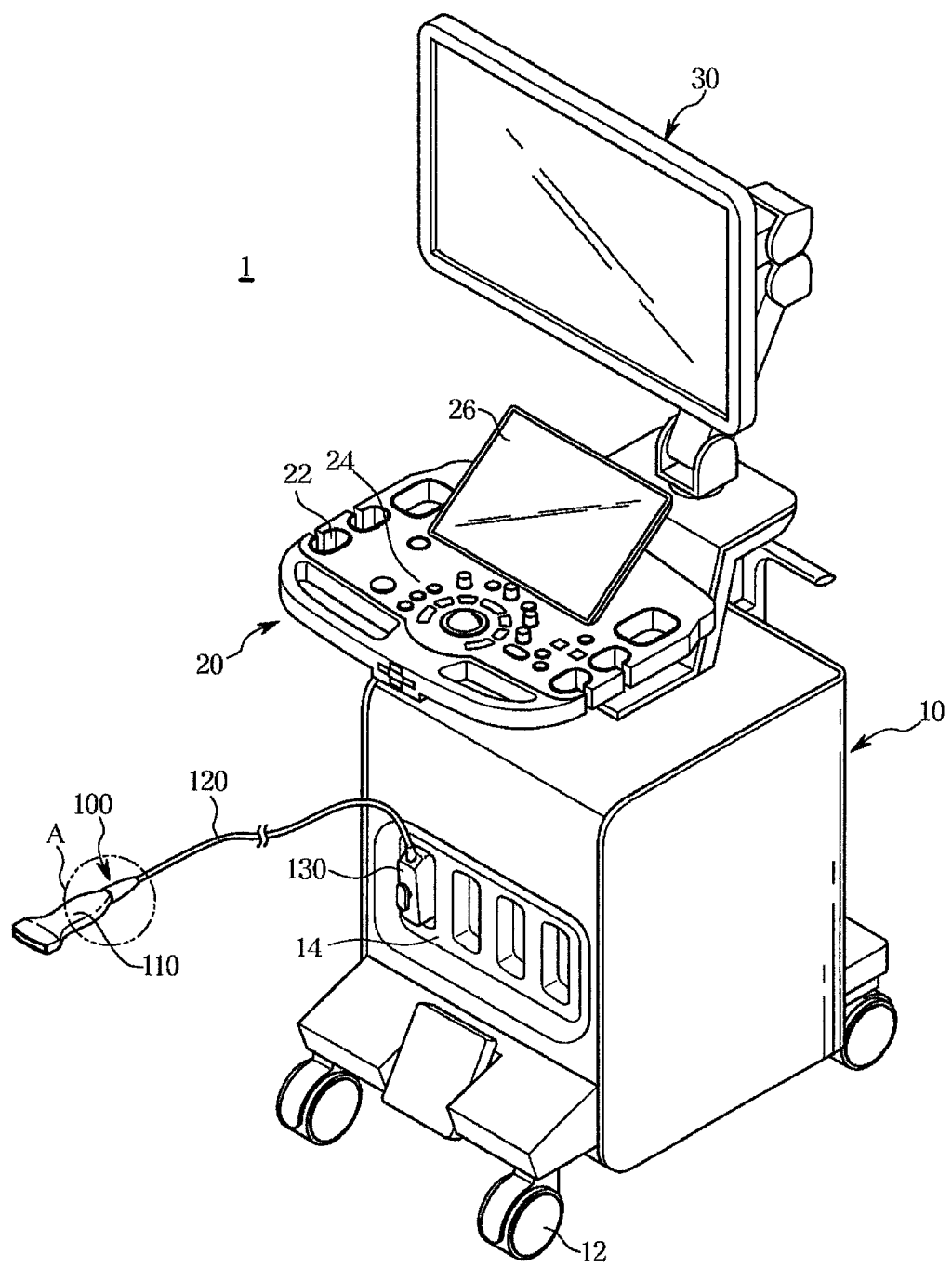
FIG. 1 is a view illustrating an ultrasonic diagnostic apparatus according to an embodiment of the disclosure.

The embodiments described in the present specification and the configurations shown in the drawings are only examples of preferred embodiments of the disclosure, and various modifications may be made at the time of filing of the disclosure to replace the embodiments and drawings of the present specification.

Like reference numerals or signs in the respective drawings of the present specification represent parts or components that perform substantially the same functions.

The terms used in the present specification are for the purpose of describing the embodiments and are not intended to restrict and/or limit the disclosure. The singular expressions herein may include plural expressions, unless the context clearly dictates otherwise. Also, the terms "comprises" and "has" are intended to indicate that there are features, numbers, steps, operations, elements, parts, or combinations thereof described in the specification, and do not exclude the presence or addition of one or more other features, numbers, steps, operations, elements, parts, or combinations thereof.

It will be understood that, although the terms "first" and "second" may be used herein to describe various components, these components is not be limited by these terms and are only used to distinguish one component from another. For example, without departing from the scope of the disclosure, the first component may be referred to as a second component, and similarly, the second component may also be referred to as a first component. The term "and/or" includes any combination of a plurality of related items or any one of a plurality of related items.

Hereinafter an ultrasonic probe according to embodiments of the disclosure will be described in detail with reference to the accompanying drawings.

FIG. 1 is a view illustrating an ultrasonic diagnostic apparatus according to an embodiment of the disclosure.

Referring to FIG. 1, an ultrasonic diagnostic apparatus 1 according to an embodiment may include a main body 10, and an ultrasonic probe 100 configured to transmit an ultrasonic signal to an object to be diagnosed and receiving a signal reflected from the object. The ultrasonic probe 100 may be connected to the main body 10 by a cable.

The ultrasonic probe 100 may be rested in the main body 10 by a holder 22. When the ultrasonic diagnostic apparatus 1 is not used, an inspector may put and store the ultrasonic probe 100 in the holder 22. Although FIG. 1 illustrates that the holder 22 in which the ultrasonic probe 100 is rested is provided on a control panel 20, the ultrasonic probe 100 may be provided on the main body 10 according to the convenience of a user. The ultrasonic probe 100 may also be provided on both of the main body 10 and the control panel 20.

The main body 10 may be provided with a moving device 12 configured to move the ultrasonic diagnostic apparatus 1. The moving device 12 may be a plurality of casters provided on a lower surface of the main body 10. The casters may be aligned to allow the main body 10 to travel in a specific direction, may be positioned to allow the main body 10 to travel in any direction, or may be locked to allow the main body 10 to stop at a specific position.

The ultrasonic probe 100 may include an ultrasonic transceiver provided in the housing 110. The ultrasonic transceiver may include a transducer module 140 configured to irradiate an ultrasonic wave to the object, to receive an echo ultrasonic wave reflected from the object, and to convert an electrical signal and the ultrasonic wave to each other. The ultrasonic probe 100 may include a male connector 130 physically coupled to a female connector 14 of the main body 10 to transmit and receive signals to and from the main body 10, and a cable 120 configured to connect the male connector 130 to the transducer module 140.

The object may be, but is not limited to, a living body of a human or animal, or an in vivo tissue such as blood vessels, bones, or muscles, and anything whose internal structure may be imaged by the ultrasonic diagnostic apparatus 1 may become an object.

The echo ultrasonic wave is an ultrasonic wave reflected from the object to which an ultrasonic wave is irradiated, and has various frequency bands or energy intensities for generating various ultrasonic images according to a diagnostic mode.

The transducer module 140 may generate an ultrasonic wave according to an applied AC power source. Specifically, the transducer module 140 may receive an AC power source from an external power supply device or an internal power storage device, for example, a battery. A vibrator of the transducer module 140 may generate ultrasonic waves by vibrating according to the supplied AC power source.

One end of the cable 120 is connected to the transducer module 140, and the other end thereof is connected to the male connector 130, so that the male connector 130 may be electrically connected to the transducer module 140. The male connector 130 may be physically coupled to the female connector 14 of the main body 10. The male connector 130 may transmit an electrical signal generated by the transducer module 140 to the female connector 14 physically coupled with the male connector 130 or receive a control signal generated in the main body 10 from the female connector 14.

Although FIG. 1 illustrates that the male connector 130 is exposed to the outside, the male connector 130 may be mounted inside a case forming the main body 10.

The main body 10 of the ultrasonic diagnostic apparatus 1 may be provided with a display 30 and the control panel 20. The control panel 20 may be provided with an input 24 to allow a user to control the ultrasonic diagnostic apparatus 1. The input 24 may receive not only setting information relating to the ultrasonic probe 100 but also various control commands from the user.

According to an embodiment, the setting information relating to the ultrasonic probe 100 includes gain information, zoom information, focus information, time gain compensation (TGC) information, depth information, frequency information, power information, frame average information, dynamic range information, and the like.

The above pieces of information may be transmitted to the ultrasonic probe 100 through the cable 120, the ultrasonic probe 100 may be set according to the received information. In addition, the main body 10 may receive various control commands, such as a command for transmitting an ultrasonic signal, through the input 24 from the user, and transmit the received control commands to the ultrasonic probe 100.

The input 24 may be provided in the form of a keyboard, a foot switch, a foot pedal, or the like. For example, the keyboard may be implemented as hardware. Such keyboard may include at least one of a switch, a key, a joystick, and a trackball. As another example, the keyboard may be implemented as software, such as a graphical user interface. In this case, the keyboard may be displayed through the display 3. The foot switch or the foot pedal may be provided at a lower portion of the main body 10, and the user may control the operation of the ultrasonic diagnostic apparatus 1 using the foot pedal.

The display 30 may be implemented in various known ways such as a cathode ray tube (CRT), a liquid crystal display (LCD), a light emitting diode (LED), a plasma display panel (PDP), and an organic light emitting diode (OLED), but is not limited thereto.

The display 30 may display an ultrasonic image of a target site within the object. The ultrasonic image displayed on the display 40 may be a 2D ultrasonic image or a 3D ultrasonic image and various ultrasonic images may be displayed according to the operation modes of the ultrasonic diagnostic apparatus 1. The display 30 may also display not only menus and information items necessary for the ultrasonic diagnosis but also information on the operation state of the ultrasonic probe 100 and the like.

According to an embodiment, the ultrasonic image includes not only an amplitude-mode (A-mode) image, a brightness mode (B-mode) image, and a motion mode (M-mode) image, but also a color-mode (C-mode) image and a Doppler-mode (D-mode) image.

The A-mode image may refer to an ultrasonic image representing the size of the ultrasonic signal corresponding to an echo ultrasonic signal, the B-mode image may refer to an ultrasonic image in which the size of the ultrasonic signal corresponding to an echo ultrasonic signal is represented by brightness, and the M-mode image may refer to an ultrasonic image that indicates the movement, of an object over time at a specific location. The D-mode image may refer to an ultrasonic image in which a moving object is represented in a waveform using the Doppler effect, and the C-mode image may refer to an ultrasonic image in which a moving object is represented in a color spectrum form.

The control panel 20 may be provided with an auxiliary display 26. The auxiliary display 26 may provide related information such as a menu or auxiliary image for optimizing the ultrasonic image or provide a graphical interface to the user.

When the auxiliary display 26 is implemented as a touch screen type, the display 30 may also perform a function of the input 24. The main body 10 may receive various commands from the user through at least one of the display 30 and the input 24. In addition, although not shown in the drawing, a voice recognition sensor may be provided in the main body 10 so that a voice command may be input from the user.

Figure 2:
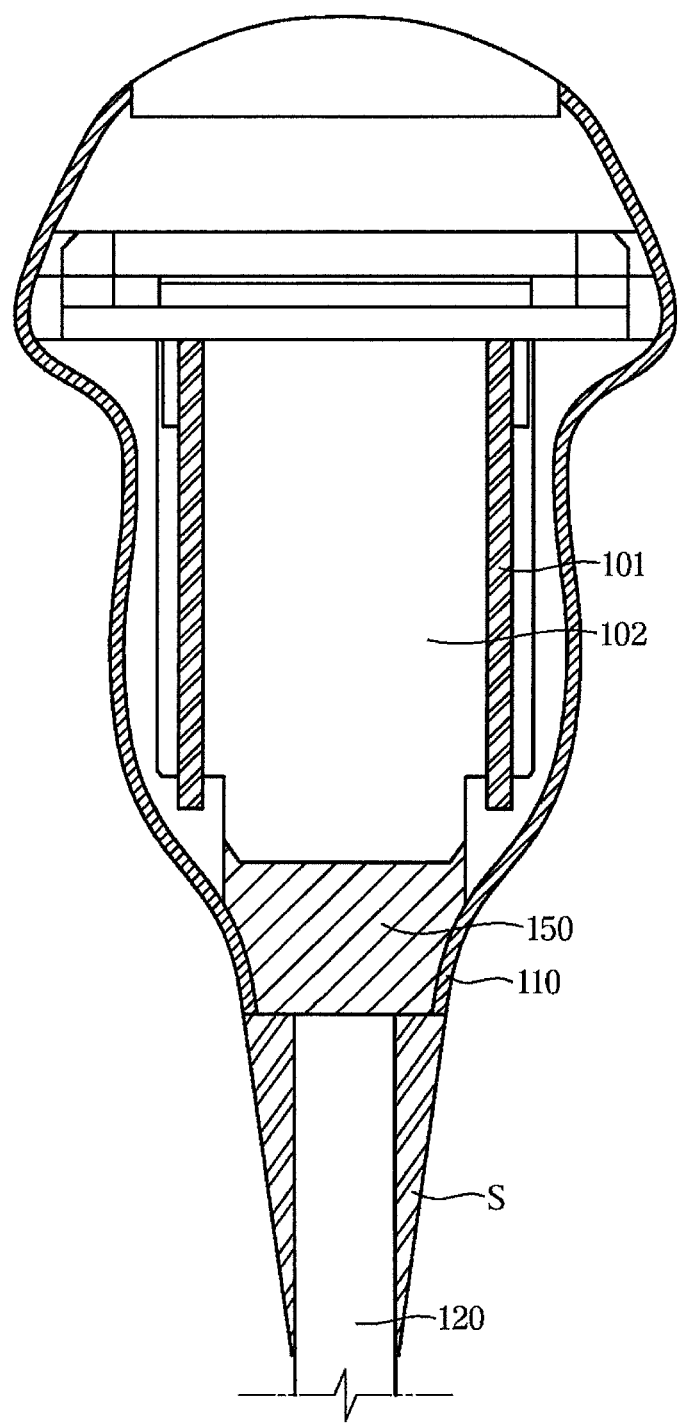
FIG. 2 is a cross-sectional view of a conventional ultrasonic probe.
Figure 3:
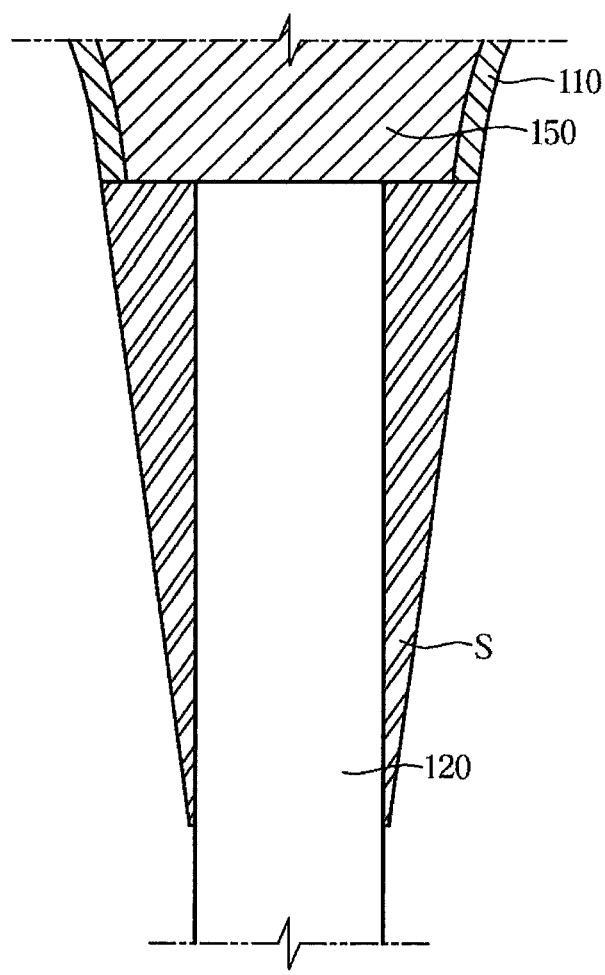
FIG. 3 is a cross-sectional view of a strain relief of the conventional ultrasonic probe.

FIG. 2 is a cross-sectional view of a conventional ultrasonic probe, and FIG. 3 is a cross-sectional view of a strain relief of the conventional ultrasonic probe.

Referring to FIG. 2, a conventional ultrasonic probe may include a transducer module therein, and a heat pipe 101 for transferring heat generated from the transducer module to a heat radiation frame 150 disposed at an inner rear of the ultrasonic probe. One end of the heat pipe 101 may be in contact with or disposed adjacent to the transducer module generating heat. The other end of the heat pipe 101 may be in contact with the heat radiation frame 150 or disposed adjacent to the heat radiation frame 150. The heat pipe 101 may be disposed adjacent to or in contact with a printed circuit board 102 to transfer heat generated from the printed circuit board 102 to the heat radiation frame 150.

Referring to FIGS. 2 and 3, the conventional ultrasonic probe includes the cable 120 and a strain relief S provided at an outer side of the cable 120 to prevent breakage of the cable 120. The conventional strain relief S is not made of a material having high thermal conductivity and does not include any structure for heat radiation. Therefore, conventionally, heat inside the ultrasonic probe may not be released to the outside of the ultrasonic probe through the strain relief S.

Figure 4:
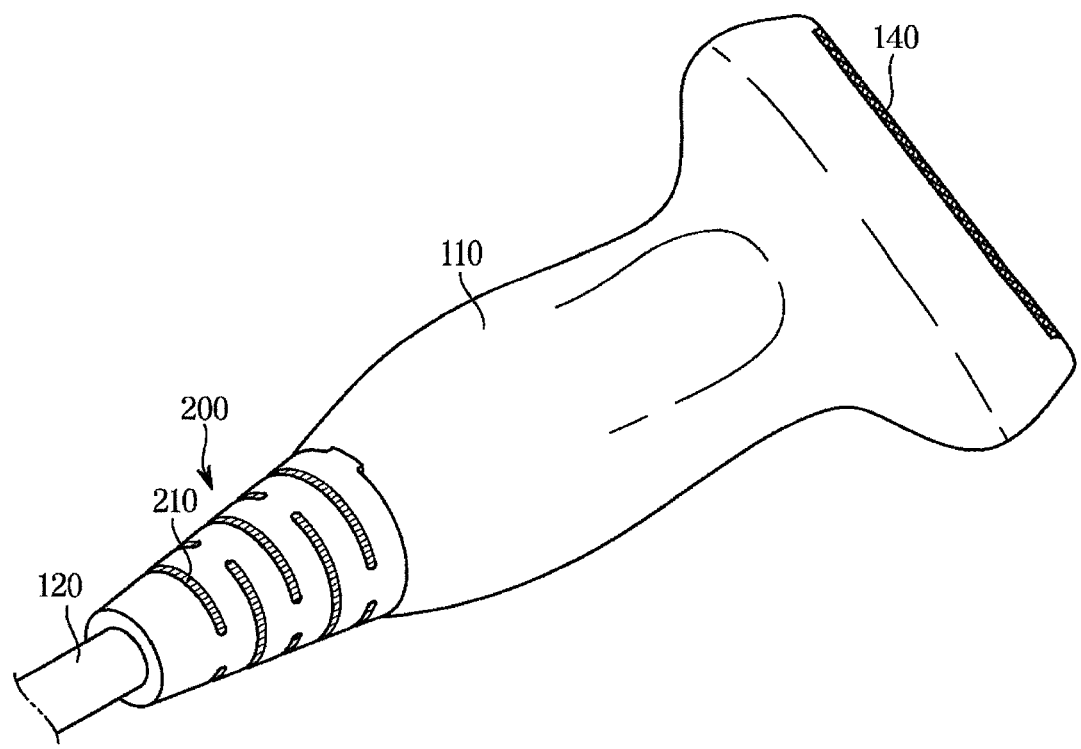
FIG. 4 is a view illustrating an ultrasonic probe according to an embodiment of the disclosure.
Figure 5:
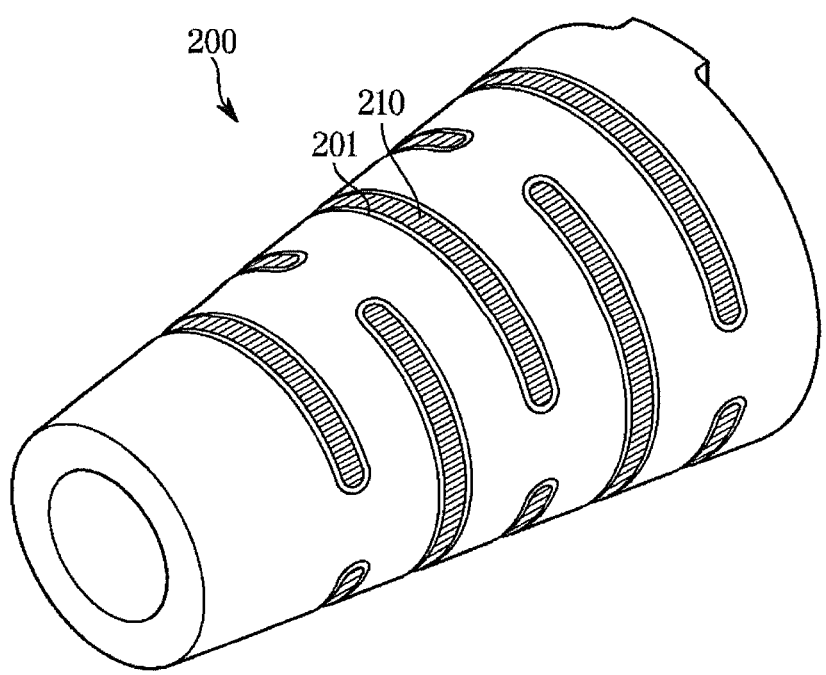
FIG. 5 is a view separately illustrating a strain relief according to an embodiment of the disclosure.

FIG. 4 is a view illustrating an ultrasonic probe according to an embodiment of the disclosure, and FIG. 5 is a view separately illustrating a strain relief according to an embodiment of the disclosure.

Referring to FIGS. 4 and 5, the ultrasonic probe 100 includes the transducer module 140, a housing 110 in which the transducer module 140 is accommodated, and the cable 120 configured to connect the transducer module 140 to the main body 10 of the ultrasonic diagnostic apparatus 1.

When the inspector uses the ultrasonic probe 100, the cable 120 may be significantly bent or twisted at an end of the housing 110 of the ultrasonic probe 100. When the cable 120 is significantly bent or twisted, the cable 120 may be disconnected. A strain relief 200 may be provided between the housing 110 and the cable 120 to prevent the cable 120 from being significantly bent or twisted at the end of the housing 110 of the ultrasonic probe 100. The strain relief 200 may be provided outside the housing 110 to prevent breakage of the cable 120.

According to an embodiment of the disclosure, the strain relief 200 may include a heat radiation groove 201 formed along a circumferential direction of the cable 120. A plurality of the heat radiation grooves 201 may be provided. The plurality of heat radiation grooves 201 may be arranged to be spaced apart along a direction in which the cable 120 extends.

The plurality of heat radiation grooves 201 may be formed along a circumferential direction of the strain relief 200. Each of the plurality of heat radiation grooves 201 may be provided not to divide the strain relief 200 in the direction in which the cable 120 extends. In other words, the strain relief 200 may not be divided in the direction in which the cable 120 extends by the heat radiation groove 201.

A heat radiation fin 210 may be disposed in each of the plurality of heat radiation grooves 201. The heat radiation fin 210 may be inserted into the heat radiation groove 201. The heat radiation fins 210 may be configured such that at least a portion thereof is in contact with outside air. The heat radiation fin 210 may release heat by coming into contact with the outside air.

Figure 6:
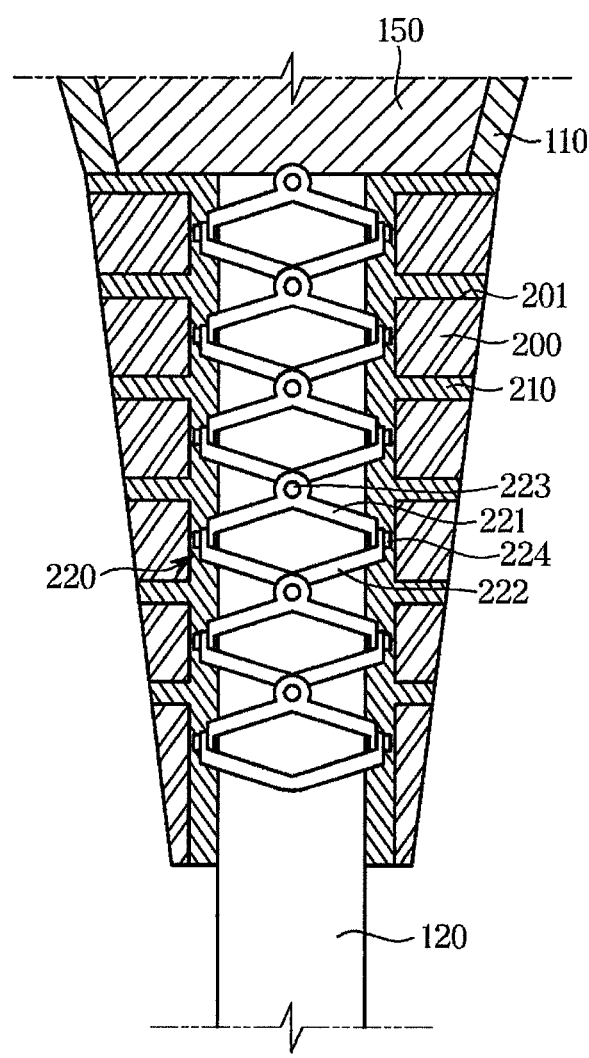
FIG. 6 is a cross-sectional view of the strain relief of the ultrasonic probe according to an embodiment of the disclosure.
Figure 7:
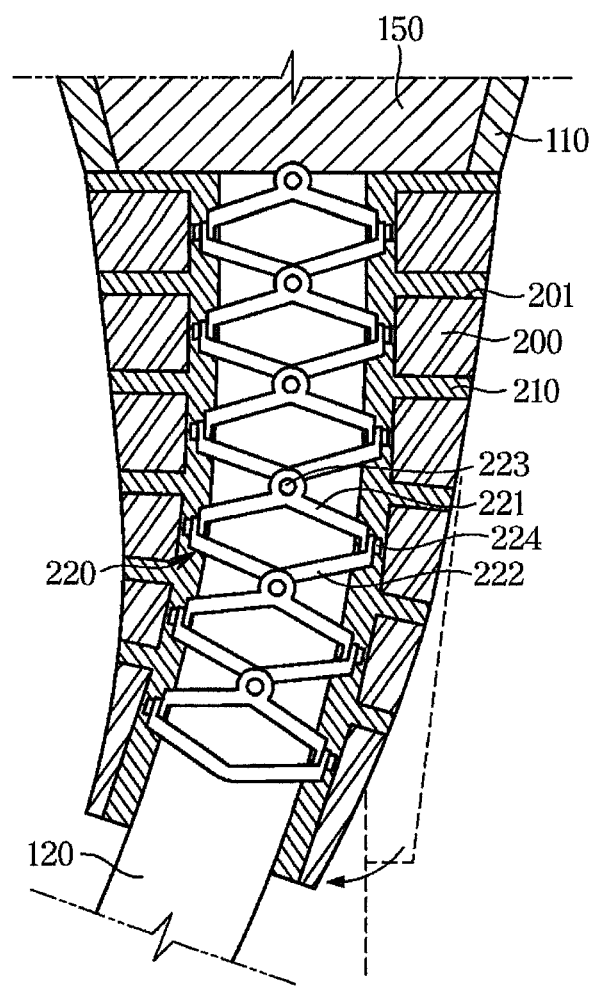
FIG. 7 is a view illustrating a state in which the strain relief illustrated in FIG. 6 is bent.

FIG. 6 is a cross-sectional view of the strain relief of the ultrasonic probe according to an embodiment of the disclosure, and FIG. 7 is a view illustrating a state in which the strain relief illustrated in FIG. 6 is bent.

The strain relief 200 according to an embodiment of the disclosure will be described in detail with reference to FIGS. 6 and 7.

As illustrated in FIG. 6, the cable 120 may be drawn out of the housing 110 through an end of the housing 110. Although not illustrated in detail in the drawing, a heat radiation frame 150 may be provided inside the housing 110. The heat radiation frame 150 may be made of a material having a high thermal conductivity. For example, the heat radiation frame 150 may be made of aluminum.

The heat radiation frame 150 may receive heat from a heat generating source disposed inside the housing 110. The heat generating source may include the transducer module 140. The heat radiation frame 150 may receive heat from the transducer module 140 through a predetermined structure, for example, a heat pipe.

When heat generated in the ultrasonic probe 100 is released to the front of the ultrasonic probe 100, the heat may cause the object to burn. To prevent this, the heat generated in the ultrasonic probe 100 is generally released to the rear of the ultrasonic probe 100.

A heat pipe (not shown) may be used to transfer heat inside the housing 110 of the ultrasonic probe 100 to the rear of the housing 110. The heat pipe may transfer heat generated in the transducer module 140 to the heat radiation frame 150 disposed in the rear of the housing 110. The heat pipe is merely an example, and the heat generated in the transducer module 140 may be transferred to the heat radiation frame 150 disposed at an inner rear of the housing 110 through various methods and structures in addition to the heat pipe.

When the heat radiation frame 150 does not release the heat transferred from the heat pipe and the like to the outside, a temperature of the heat radiation frame 150 disposed inside the housing 110 continuously increases. Therefore, even though the heat radiation frame 150 is included, the heat radiation effect of the heat radiation frame 150 is insignificant when the ultrasonic probe 100 is used for a long time. For this reason, in order to improve the heat radiation performance of the ultrasonic probe 100, a heat radiation structure for releasing heat inside the housing 110 to the outside of the housing 110 is required.

According to an embodiment of the disclosure, the ultrasonic probe 100 may release heat inside the housing 110 to the outside of the housing 110 through the strain relief 200. By releasing the heat inside the housing 110 to the outside, the heat radiation capability of the ultrasonic probe 100 may be improved.

Referring to FIG. 6, the ultrasonic probe 100 may include a bending device 220 configured to surround the cable 120.

The bending device 220 may be configured to be bendable in two directions crossing each other. For example, the bending device 220 may be bent in the front-rear direction and may be bent in the left and right directions. Because the bending device 220 may be bent in two directions, the bending device 220 does not interfere with the bending of the cable 120. Even when the bending device 220 is coupled to cover the outer surface of the cable 120, the cable 120 may be bent in the left and right directions and the front and rear directions. Therefore, even when the cable 120 is coupled to the bending device 220, the cable 120 may be bent like the conventional one.

The bending device 220 may include a first bending member 221 and a second bending member 222 rotatably coupled to the first bending member 221. The first bending member 221 and the second bending member 222 may each include a hollow portion through which the cable 120 passes. A plurality of the first bending members 221 and a plurality of the second bending members 222 may be provided. The plurality of first bending members 221 and the plurality of second bending members 222 may be repeatedly coupled to each other. The first bending members 221 and the second bending members 222 may be repeatedly coupled to each other along the direction in which the cable 120 extends.

Referring to FIG. 6, the first bending member 221 and the second bending member 222 disposed below the first bending member 221 may be coupled to be rotatable in a first direction. In addition, the second bending member 222 and the first bending member 221 disposed below the second bending member 222 may be coupled to be rotatable in a second direction. The first direction and the second direction may cross each other. For example, the first direction may be referred to the front and rear directions, and the second direction may be referred to the left and right directions.

Referring to FIG. 6, the first bending member 221 and the second bending member 222 may be rotatably coupled to a first rotation shaft 223 to be rotated in the first direction. The first bending member 221 and the second bending member 222 may be rotatably coupled to the pair of first rotation shafts 223. The cable 120 may be disposed between the pair of first rotation shafts 223.

Likewise, the second bending member 222 and the first bending member 221 may be rotatably coupled to a second rotation shaft 224 to be rotated in the second direction crossing the first direction. The second bending member 222 and the first bending member 221 may be rotatably coupled to the pair of second rotation shafts 224. The cable 120 may be disposed between the pair of second rotation shafts 224.

The bending device 220 may be made of a material having a high thermal conductivity. For example, the bending device 220 may be made of aluminum. Because the bending device 220 is made of a material having a high thermal conductivity, the bending device 220 may easily receive heat from the heat radiation frame 150. That is, heat of the heat radiation frame 150 may be quickly transferred to the bending device 220.

Heat transferred from the heat radiation frame 150 to the bending device 220 may be released to the outside of the strain relief 200 through the heat radiation fin 210. As described above, the strain relief 200 may include the heat radiation groove 201, and the heat radiation fin 210 may be provided in the heat radiation groove 201. The heat radiation fins 210 may be configured to be in contact with the bending device 220. One end of the heat radiation fin 210 may be in contact with the bending device 220 to receive heat from the bending device 220. The heat radiation fin 210 may transfer heat received from the bending device 220 to outside air by the other end thereof coming into contact with the outside air. Therefore, according to an embodiment of the disclosure, heat generated inside the ultrasonic probe 100 may be released to the outside of the ultrasonic probe 100 through the heat radiation frame 150, the bending device 220, and the heat radiation fin 210. Specifically, heat generated inside the ultrasonic probe 100 may be released to the outside of the strain relief 200 through the heat radiation groove 201 of the strain relief 200.

Unlike the conventional ultrasonic probe, the ultrasonic probe 100 according to an embodiment of the disclosure may provide more direct heat radiation in that heat inside the ultrasonic probe 100 may be released through the heat radiation fin 210 being directly in contact with the outside. Through this, the heat radiation capability of the ultrasonic probe 100 according to an embodiment of the disclosure may be improved.

Referring to FIG. 7, in the ultrasonic probe 100 according to an embodiment of the disclosure, the cable 120, the bending device 220 configured to surround the cable 120, the heat radiation fin 210, and the strain relief 200 may be bent. As is known, the cable 120 may be made of a flexible material capable of being bent. The strain relief 200 may also be made of a flexible material capable of being bent. Because the strain relief 200 is intended to prevent disconnection due to a significant bending of the cable 120, the strain relief 200 may be configured to prevent the significant bending of the cable 120 while being able to be flexibly bent. To this end, the strain relief 200 may be provided in a substantially truncated cone shape. The strain relief 200 may be configured such that a thickness thereof becomes thicker as the strain relief 200 is closer to the housing 110. The strain relief 200 may be thinner as the strain relief 200 is farther from the housing 110.

Although FIG. 7 illustrates that the strain relief 200 is bent to the left side of the drawing, the strain relief 200 may be bent to the right side of the drawing and may be bent to the front and the rear of the drawing. That is, the strain relief 200 and the cable 120 in the ultrasonic probe 100 according to the embodiment of the disclosure may be bent freely like the conventional ones. Therefore, while maintaining the flexible characteristics of the strain relief 200, the heat inside the ultrasonic probe 100 may be released to the outside through the heat radiation fin 210, thereby increasing the heat radiation efficiency.

Figure 8:
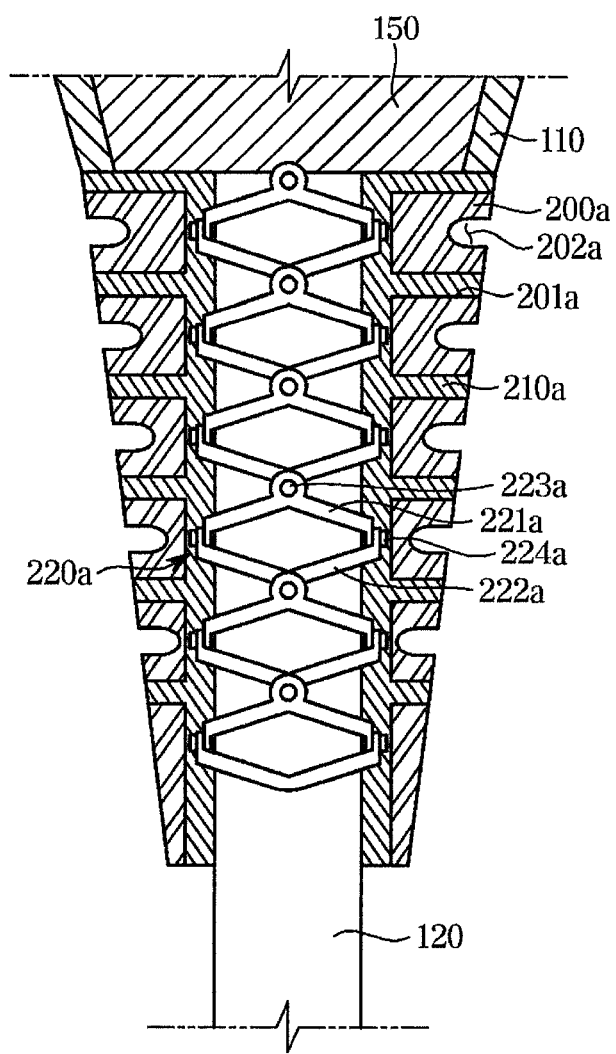
FIG. 8 is a cross-sectional view of a strain relief of an ultrasonic probe according to another embodiment of the disclosure.

FIG. 8 is a cross-sectional view of a strain relief of an ultrasonic probe according to another embodiment of the disclosure.

Hereinafter a strain relief 200a of the ultrasonic probe according to another embodiment of the disclosure will be described with reference to FIG. 8. The content duplicated with the content described above will be omitted.

Referring to FIG. 8, the strain relief 200a according to another embodiment of the disclosure may further include a bending groove 202a to improve bending capability.

As illustrated in FIG. 8, the strain relief 200a may include the bending groove 202a on an outer surface thereof. The bending groove 202a may improve the flexibility of the strain relief 200a. Because the strain relief 200a according to another embodiment of the disclosure is made of a flexible material but further includes a bending device and a heat radiation fin therein, the strain relief 200a may have a lower flexibility than the conventional strain relief. According to another embodiment of the disclosure, the bending capability of the strain relief 200a may be improved by the bending groove 202a formed in the outer surface of the strain relief 200a.

Figure 9:
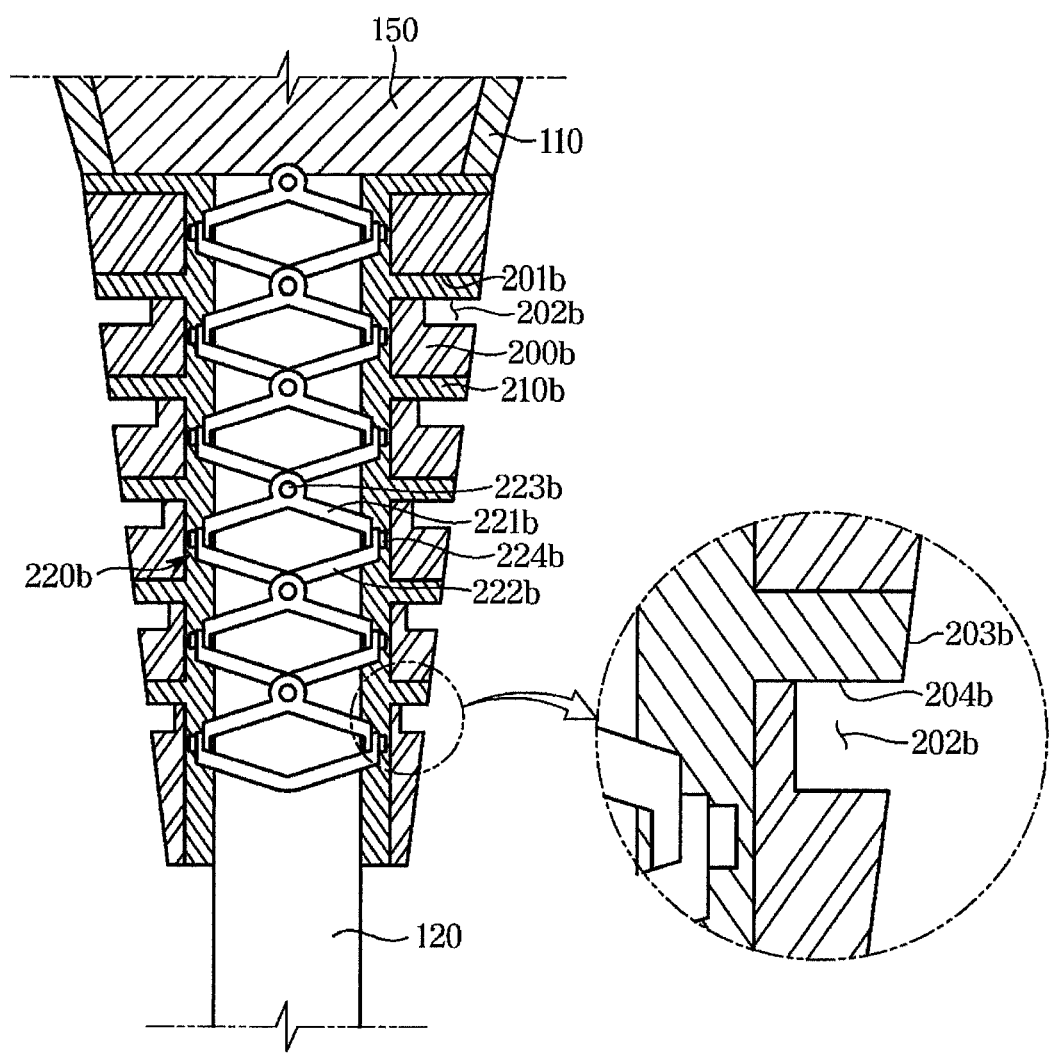
FIG. 9 is a cross-sectional view of a strain relief of an ultrasonic probe according to another embodiment of the disclosure.

FIG. 9 is a cross-sectional view of a strain relief of an ultrasonic probe according to another embodiment of the disclosure.

Referring to FIG. 9, a strain relief 200b according to another embodiment of the disclosure may further include a cutout portion 202b to improve heat radiation capability.

As illustrated in FIG. 9, the strain relief 200b may include the cutout portion 202b formed by cutting a portion of a heat radiation groove 201b. The cutout portion 202b may be formed by recessing one surface of the heat radiation groove 201b.

The cutout portion 202b may increase a contact area between a heat radiation fin 210b and outside air. The heat radiation fin 210b may include a first contact portion 203b and a second contact portion 204b. The first contact portion 203b may refer to a side surface portion of the heat radiation fin 210b. The second contact portion 204b may refer to a lower surface portion of the heat radiation fin 210b. According to an embodiment, in addition to the first contact portion 203b of the heat radiation fin 210b, the second contact portion 204b may also be in contact with outside air. In other words, in addition to the side surface of the heat radiation fin 210b, the lower surface of the heat radiation fin 210b may also be in contact with outside air. When the cutout portion 202b is not provided, the heat radiation fin 210b may exchange heat with outside air only through the first contact portion 203b. According to another embodiment of the disclosure, by forming the cutout portion 202b, the heat radiation fin 210b may exchange heat with outside air through the second contact portion 204b as well as the first contact portion 203b. In other words, the heat radiation fin 210b may exchange heat with outside air through the side and lower surfaces of the heat radiation fin 210b. Through this, the heat radiation capability of the heat radiation fin 210b may be improved, and thus the heat radiation capability of the ultrasonic probe may be improved.

Figure 10:
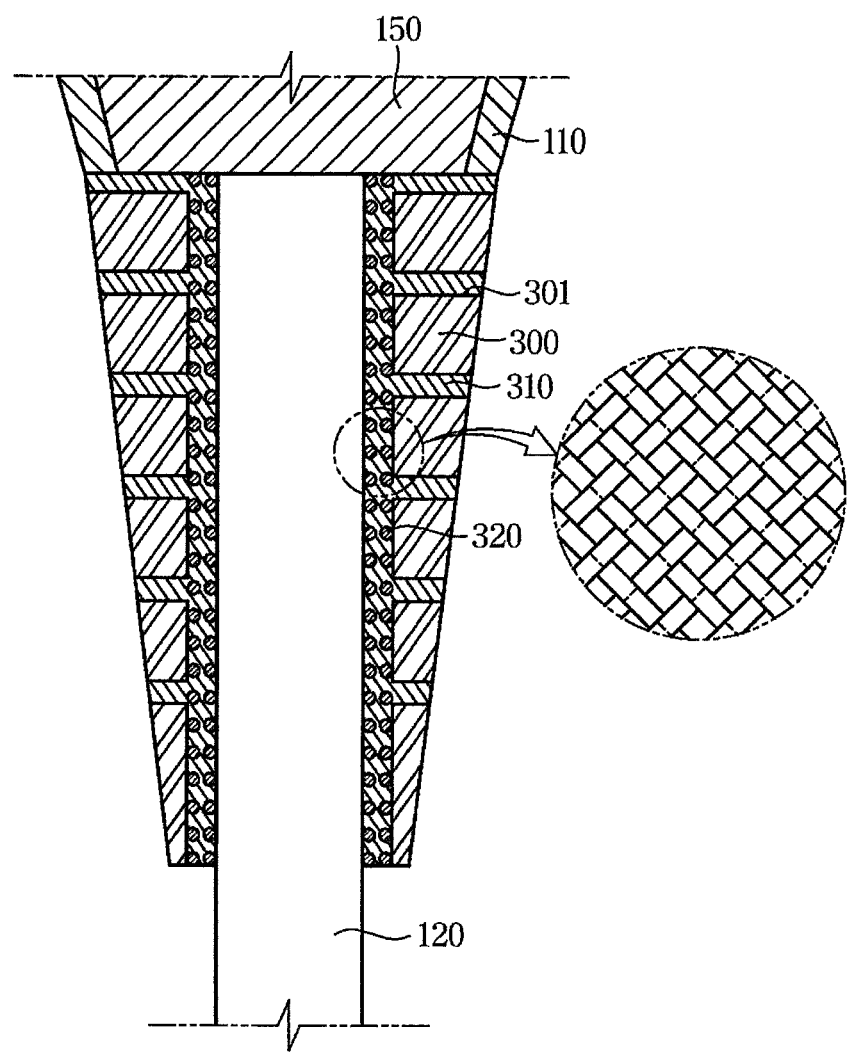
FIG. 10 is a cross-sectional view of a strain relief of an ultrasonic probe according to another embodiment of the disclosure.

FIG. 10 is a cross-sectional view of a strain relief of an ultrasonic probe according to another embodiment of the disclosure.

Referring to FIG. 10, in an ultrasonic probe according to another embodiment of the disclosure, a strain relief 300 may include a mesh member 320. The mesh member 320 may be made of a material having a high thermal conductivity. For example, the mesh member 320 may be formed of a metal material.

The mesh member 320 may be configured to be bendable in various directions due to its structural characteristics. The mesh member 320 may be configured to be bendable within a predetermined range regardless of the direction. In addition, because the mesh member 320 is formed of a material having a high thermal conductivity, the mesh member 320 may have a high thermal conductivity.

According to another embodiment of the disclosure, the mesh member 320 may be configured to surround the outer surface of the cable 120. The mesh member 320 may be configured such that one end thereof is in contact with the heat radiation frame 150. An outer surface of the mesh member 320 may be coupled to the strain relief 300, and the strain relief 300 may include a heat radiation groove 301 and a heat radiation fin 310 inserted into the heat radiation groove 301. The heat radiation fin 310 may be disposed such that one end thereof is in contact with the mesh member 320 and the other end thereof is in contact with outside air. By this arrangement, heat in the heat radiation frame 150 may be transferred to the mesh member 320 and may be transferred from the mesh member 320 to the outside air through the heat radiation fin 310. Heat in the heat radiation frame 150 may be released to the outside of the strain relief 300 via the mesh member 320 and the heat radiation fin 310. Because the heat radiation fin 310 is in direct contact with the outside air, as described above, heat may be effectively released to the outside, and the heat radiation capability of the ultrasonic probe may be improved.

Figure 11:
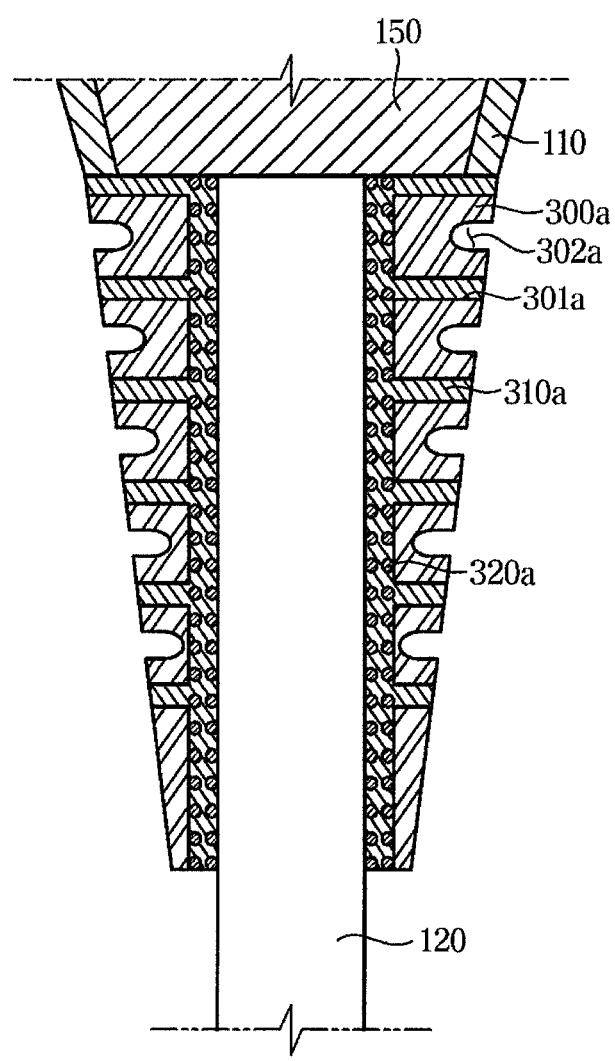
FIG. 11 is a cross-sectional view of a strain relief of an ultrasonic probe according to another embodiment of the disclosure.

FIG. 11 is a cross-sectional view of a strain relief of an ultrasonic probe according to another embodiment of the disclosure.

Referring to FIG. 11, a strain relief 300a according to another embodiment of the disclosure may further include a bending groove 302a to improve bending capability.

As illustrated in FIG. 11, the strain relief 300a may include a bending groove 302a on an outer surface thereof. The bending groove 302a may improve the flexibility of the strain relief 300a. Because the strain relief 300a according to another embodiment of the disclosure is made of a flexible material but further includes a bending device and a heat radiation fin therein, the strain relief 300a may have a lower flexibility than the conventional strain relief. According to another embodiment of the disclosure, the bending capability of the strain relief 300a may be improved by the bending groove 302a formed in the outer surface of the strain relief 300a.

Figure 12:
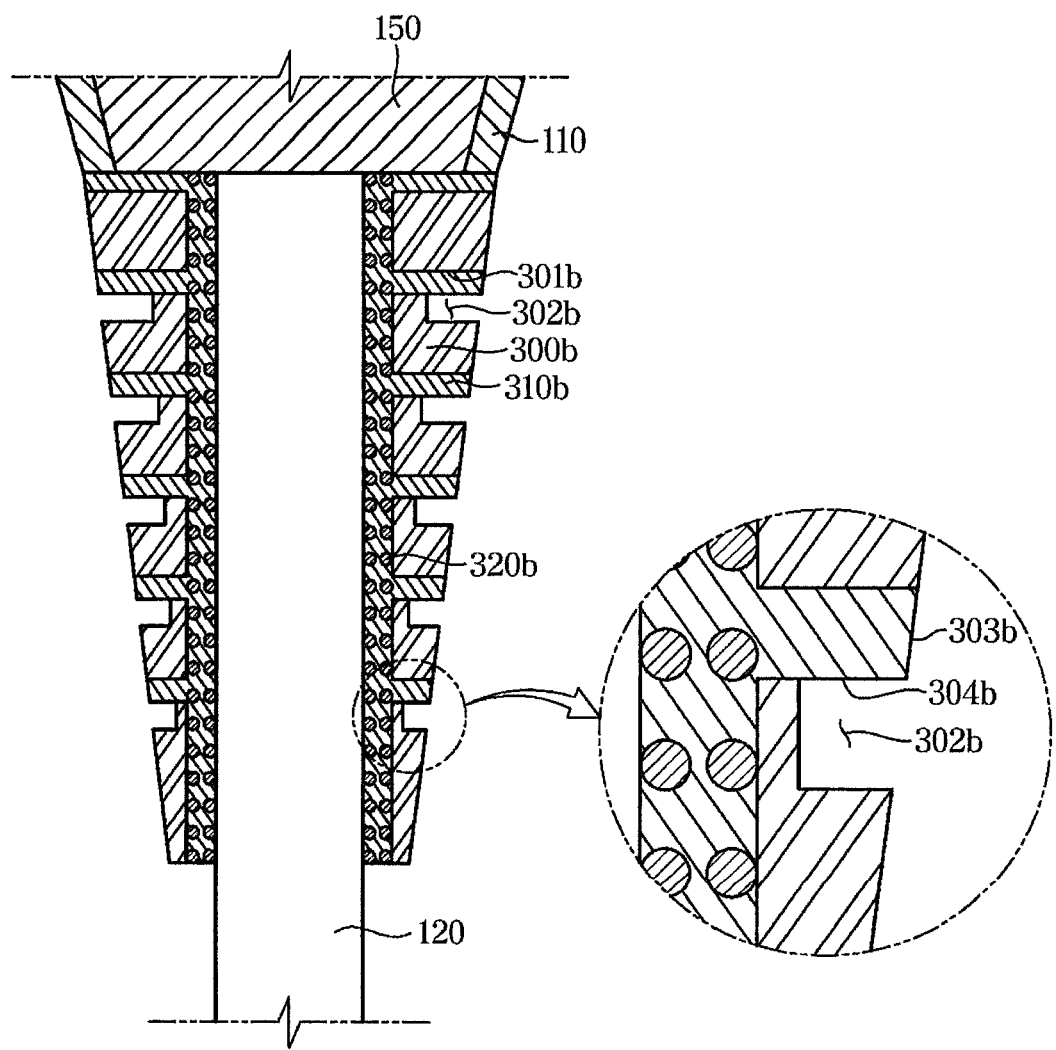
FIG. 12 is a cross-sectional view of a strain relief of an ultrasonic probe according to another embodiment of the disclosure.

FIG. 12 is a cross-sectional view of a strain relief of an ultrasonic probe according to another embodiment of the disclosure.

As illustrated in FIG. 12, a strain relief 300b may include the cutout portion 302b formed by cutting a portion of a heat radiation groove 301b. The cutout portion 302b may be formed by recessing one surface of the heat radiation groove 301b.

The cutout portion 302b may increase a contact area between a heat radiation fin 310b and outside air. The heat radiation fin 310b may include a first contact portion 303b and a second contact portion 304b. The first contact portion 303b may refer to a side surface portion of the heat radiation fin 310b. The second contact portion 304b may refer to a lower surface portion of the heat radiation fin 310b. According to an embodiment, in addition to the first contact portion 303b of the heat radiation fin 310b, the second contact portion 304b may also be in contact with outside air. In other words, in addition to the side surface of the heat radiation fin 310b, the lower surface of the heat radiation fin 310b may also be in contact with outside air. When the cutout portion 302b is not provided, the heat radiation fin 310b may exchange heat with outside air only through the first contact portion 303b. According to another embodiment of the disclosure, by forming the cutout portion 302b, the heat radiation fin 310b may exchange heat with outside air through the second contact portion 304b as well as the first contact portion 303b. In other words, the heat radiation fin 310b may exchange heat with outside air through the side and lower surfaces of the heat radiation fin 310b. Through this, the heat radiation capability of the heat radiation fin 310b may be improved, and thus the heat radiation capability of the ultrasonic probe may be improved.

As is apparent from the above, according to an embodiment of the disclosure, an ultrasonic probe having an improved heat radiation capability can be provided.

According to an embodiment of the disclosure, because a heat radiation groove is formed in a strain relief and a heat radiation fin is disposed in the heat radiation groove, the ultrasonic probe having the heat radiation capability improved by the heat radiation fin while maintaining the flexible characteristics of the strain relief can be provided.

While the disclosure has been particularly described with reference to exemplary embodiments, it should be understood by those of skilled in the art that various changes in form and details may be made without departing from the spirit and scope of the disclosure.

What is claimed is:

1. An ultrasonic probe comprising:
   a transducer module configured to transmit and receive an ultrasonic signal;
   a housing configured to accommodate the transducer module;
   a cable connected to the transducer module inside the housing and drawn from the inside of the housing to the outside of the housing through an end of the housing;
   a bending device configured to cover the cable and connected to the end of the housing to receive heat;
   a strain relief configured to surround the bending device and including a heat radiation groove extending along a circumferential direction of the cable and connecting an inside and an outside of the strain relief to each other; and
   a heat radiation fin accommodated inside the strain relief and penetrating the strain relief along the heat radiation groove such that one end thereof is in contact with the bending device and the other end thereof is in contact with outside air.

2. The ultrasonic probe according to claim 1, wherein the bending device is configured to be bendable in a first direction and in a second direction crossing the first direction.

3. The ultrasonic probe according to claim 1, wherein the bending device and the heat radiation fin are configured to have a higher thermal conductivity than the strain relief.

4. The ultrasonic probe according to claim 1, wherein the strain relief is made of a flexible material to be bendable in all radial directions.

5. The ultrasonic probe according to claim 1, further comprising
   a heat radiation frame disposed inside the housing and adjacent to the end of the housing and configured to receive heat generated in the housing.

6. The ultrasonic probe according to claim 5, wherein the bending device is disposed such that at least a portion thereof is in contact with the heat radiation frame.

7. The ultrasonic probe according to claim 1, wherein the strain relief further includes a cutout portion formed on one surface of the heat radiation groove to increase a contact area between the heat radiation fin and outside air.

8. The ultrasonic probe according to claim 1, wherein the strain relief further includes a bending groove formed by recessing a portion of an outer surface of the strain relief to enhance the flexibility of the strain relief.

9. The ultrasonic probe according to claim 1, wherein the bending device includes
a first bending member including a hollow portion through which the cable passes, and
a second bending member including a hollow portion through which the cable passes and coupled to the first bending member to be rotatable in a first direction and in a second direction crossing the first direction with respect to the first bending member.

10. The ultrasonic probe according to claim 9, wherein the first bending member and the second bending member are repeatedly arranged along a direction in which the cable extends.

11. An ultrasonic probe comprising:
a transducer module configured to transmit and receive an ultrasonic signal;
a housing configured to accommodate the transducer module;
a cable connected to the transducer module inside the housing and drawn from the inside of the housing to the outside of the housing through an end of the housing;
a mesh member configured to surround the cable and to be bendable in all radial directions;
a strain relief configured to surround an outer surface of the mesh member and including a heat radiation groove extending along a circumferential direction of the cable and connecting an inside and an outside of the strain relief to each other; and
a heat radiation fin accommodated inside the strain relief and penetrating the strain relief along the heat radiation groove such that one end thereof is in contact with the mesh member and the other end thereof is in contact with outside air.

12. The ultrasonic probe according to claim 11, further comprising
a heat radiation frame disposed inside the housing and adjacent to the end of the housing and configured to receive heat generated in the housing.

13. The ultrasonic probe according to claim 12, wherein the mesh member is disposed such that at least a portion thereof is in contact with the heat radiation frame.

14. The ultrasonic probe according to claim 11, wherein the strain relief further includes a cutout portion formed on one surface of the heat radiation groove to increase a contact area between the heat radiation fin and outside air.

15. The ultrasonic probe according to claim 11, wherein the strain relief further includes a bending groove formed by recessing a portion of an outer surface of the strain relief to enhance the flexibility of the strain relief.

16. The ultrasonic probe according to claim 11, wherein the mesh member and the heat radiation fin are made of a metal material to have a higher thermal conductivity than the strain relief.

17. The ultrasonic probe according to claim 11, wherein the strain relief is made of a flexible material to be bendable in all radial directions.

* * * * *